United States Patent
Qian et al.

(10) Patent No.: US 10,018,615 B2
(45) Date of Patent: Jul. 10, 2018

(54) THREE-DIMENSIONAL ELECTRONIC SCAFFOLD FOR CARDIAC APPLICATIONS

(71) Applicant: Lawrence Livermore National Security, LLC, Livermore, CA (US)

(72) Inventors: Fang Qian, Santa Cruz, CA (US); Mihail Bora, Livermore, CA (US); Eric Duoss, Dublin, CA (US); Christopher Spadaccini, Oakland, CA (US); Cheng Zhu, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 118 days.

(21) Appl. No.: 15/064,044

(22) Filed: Mar. 8, 2016

(65) Prior Publication Data

US 2017/0261487 A1   Sep. 14, 2017

(51) Int. Cl.
| | |
|---|---|
| *G01L 1/04* | (2006.01) |
| *C12N 5/077* | (2010.01) |
| *G01N 33/48* | (2006.01) |
| *G01N 33/483* | (2006.01) |
| *G01N 33/50* | (2006.01) |

(52) U.S. Cl.
CPC ....... *G01N 33/4833* (2013.01); *C12N 5/0657* (2013.01); *G01N 33/5082* (2013.01); *C12N 2513/00* (2013.01); *C12N 2533/00* (2013.01); *C12N 2533/30* (2013.01)

(58) Field of Classification Search
USPC .................................. 73/760, 783, 862.636
See application file for complete search history.

(56) References Cited

U.S. PATENT DOCUMENTS

2003/0153965 A1   8/2003   Supronowicz et al.

FOREIGN PATENT DOCUMENTS

| KR | 10-1540845 B1 | 7/2015 |
|---|---|---|
| WO | WO-2014/120952 A1 | 8/2014 |
| WO | WO-2015/013210 A1 | 1/2015 |
| WO | WO-2015/061907 A1 | 5/2015 |

OTHER PUBLICATIONS

Baharvand et al., "Differentiation of human embryonic stem cells into hepatocytes in 2D and 3D culture systems in vitro", Int J Dev Biol, vol. 50, No. 7, 2006, pp. 645-652.
Bhana et al., "Influence of substrate stiffness on the phenotype of heart cells", Biotechnology Bioengineering, vol. 105, No. 6, 2010, pp. 1148-1160.
Duan et al., Nanoelectronics-biology frontier: From nanoscopic probes for action potential recording in live cells to three-dimensional cyborg tissues, Nano Today, vol. 8, 2013, pp. 351-373.
Jakus et al., "Three Dimensional Printing of High-Content Graphene Scaffolds for Electronic and Biomedical Applications", ACS Nano, 2015, pp. 90-128.
Kawaguchi et al., "3D-Culture System for Heart Regeneration and Cardiac Medicine" BioMed Res Inst, 2013, pp. 1-6.
Liu et al., "Improved Dispersion of Carbon Nanotubes in Polymers at High Concentrations", Nanomaterials, vol. 2, 2012, pp. 329-347.
Muth et al., "Embedded 3D Printing of Strain Sensors within Highly Stretchable Elastomers", Advanced Materials, vol. 26, 2014, pp. 6307-6312.
Pampaloni et al., "The third dimension bridges the gap between cell culture and live tissue", Nat Rev Mol Cell Biol, vol. 8, No. 10, 2007, pp. 839-845.
Pfister et al., "Regenerative therapy for cardiovascular disease", Transl Res, vol. 163, vol. 4, 2014, pp. 307-320.
Sullivan et al. "Electrophoretic Deposition of Thermites onto Micro-Engineered Electrodes Prepared by Direct-Ink Writing", The Journal of Physical Chemistry, B 117, 1686, 2013.
Tian et al., "Macroporous nanowire nanoelectronic scaffolds for synthetic tissues," Nat Mater, vol. 11, No. 11, 2012, pp. 986-994.
Timko et al., "Electrical recording from hearts with flexible nanowire device arrays", Nano Letters, vol. 9, No. 2, 2009, pp. 914-918.
Unno et al., "Side population cells: moving toward the center stage of cardiac regeneration", Circ Res., vol. 110, No. 10, 2012, pp. 1355-1363.
Xu et al., "Assembly of Micro/nanomaterials into Complex, Three-Dimensional Architectures by Compressive Buckling", Science, vol. 347, 2015, pp. 154-159.
Bosi et al., "From 2D to 3D: novel nanostructured scaffold to investigate signaling in reconstructed neuronal networks," Science Reports, vol. 5, No. 9562, Apr. 24, 2015, pp. 1-11.
Zhu et al., Supercapacitors Based on Three-Dimensional Hierarchical Graphene Aerogels with Periodic Macropores, Nano Letters, vol. 16, No. 6, Jan. 20, 2015, pp. 3448-3456.
International Search Report and Written Opinion issued in corresponding application No. PCT/US2017/017808 dated May 25, 2017.

*Primary Examiner* — Allison M Fox
(74) *Attorney, Agent, or Firm* — Foley & Lardner, LLP

(57) ABSTRACT

Disclosed here is a three-dimensional electronic scaffold, comprising a porous scaffold and a plurality of micro-strain gauges distributed spatially inside the porous scaffold, wherein the micro-strain gauges are adapted to detect contraction force. Also disclosed is a method comprising detecting and mapping intra-tissue cardiac contraction force of one or more cardiac cells or tissues disposed in a three-dimensional electronic scaffold, wherein the three-dimensional electronic scaffold comprises a porous scaffold and a plurality of micro-strain gauges distributed spatially inside the porous scaffold and in contact with the cardiac cells or tissues, and wherein the micro-strain gauges are adapted to detect contraction force of the cardiac cells or tissues.

19 Claims, 3 Drawing Sheets

THREE-DIMENSIONAL ELECTRONIC SCAFFOLD FOR CARDIAC APPLICATIONS

STATEMENT AS TO RIGHTS TO INVENTIONS MADE UNDER FEDERALLY SPONSORED RESEARCH AND DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

As an alternative to animal testing, in vitro cell culture is a powerful technique in biomedical research to probe tissue functions, intercellular communications as well as cellular responses to environmental stimuli such as drugs and toxins. Recently, 3D in vitro culture (e.g., where cells are cultured in a porous scaffold and grown into a 3D tissue) has shown cellular physiology and functions that resemble in vivo cells and tissues, in contrast to conventional 2D culture (e.g., where cells are cultured on a petri dish and grown into a monolayer). See Pampaloni et al., *Nature Review: Mol. Cell Biol.*, 8:839-845 (2007); Kawaguchi et al., *BioMed. Research Int'l*, 895967 (2013); Bahavand et al., *Int'l Dev. Biol.*, 50:645-652 (2006). For example, maturation markers were more readily observed in 3D-cultured embryonic cardiomyocytes, and 3D scaffolds can often help retain contractile functions of the developing embryonic myocardium.

However, prevailing 3D scaffolds lack the ability to monitor cellular functions. Characterization of 3D-cultured cells still relies on digestion of the cultured cells followed by biochemical assays, histology assays, or other downstream assays, which are laborious and often lead to cell death.

SUMMARY

Disclosed here is a novel three-dimensional electronic scaffold (3DES) that not only facilitate the generation of in vivo-like tissues, but also is capable of recording physiological functions in real time. The 3DES can map intratissue cardiac contraction force and thus can assist mechanistic studies in fundamental cardiac research, pharmaceutical development, and regenerative medicine.

Therefore, one aspect of some embodiments of the invention described herein relates to a three-dimensional electronic scaffold, comprising a porous scaffold and a plurality of micro-strain gauges distributed spatially inside the porous scaffold, wherein the micro-strain gauges are adapted to detect contraction force.

In some embodiments, the porous scaffold comprises a biocompatible material. In some embodiments, the porous scaffold comprises silicone. In some embodiments, the porous scaffold comprises hydrogel. In some embodiments, the porous scaffold comprises fluorine rubber.

In some embodiments, the porous scaffold has a Young's modulus of about 1 kPa to about 30 kPa. In some embodiments, the porous scaffold has a Young's modulus of about 5 kPa to about 20 kPa. In some embodiments, the porous scaffold has a Young's modulus of about 10 kPa to about 15 kPa.

In some embodiments, the porous scaffold has a porosity of about 20-80%, or about 20-40%, or about 40-60%, or about 60-80%. In some embodiments, the mechanical properties of the porous scaffold can be tailored to match the stiffness of natural cardiac tissues.

In some embodiments, the micro-strain gauges are composed of a conductive ink. In some embodiments, the micro-strain gauges are obtainable or obtained by direct ink writing using a conductive ink. In some embodiments, the micro-strain gauges are obtainable or obtained by 3D printing using a conductive ink. In some embodiments, the micro-strain gauges comprise a conductive silicone composite. In some embodiments, the micro-strain gauges comprise a conductive fluorine rubber composite.

In some embodiments, the micro-strain gauges comprise a conductive silicone composite loaded with a conductive nanomaterial. In some embodiments, the micro-strain gauges comprise a conductive silicone composite loaded with carbon nanofiber. In some embodiments, the micro-strain gauges comprise a conductive silicone composite loaded with at least about 1.5 wt. %, or at least about 2%, or at least about 3%, or at least about 4%, or at least about 5% of carbon nanofiber. In some embodiments, the micro-strain gauges comprise a conductive silicone composite loaded with about 1-30 wt. %, or about 1.5-20 wt. %, or about 1.5-10 wt. %, or about 2-5 wt. % of carbon nanofiber.

In some embodiments, the micro-strain gauges comprise a conductive silicone composite loaded with silver nanoparticles. In some embodiments, the micro-strain gauges comprise a conductive silicone composite loaded with silver nanopowder. In some embodiments, the micro-strain gauges comprise a conductive silicone composite loaded with silver nano-flakes. In some embodiments, the micro-strain gauges comprise a conductive silicone composite loaded with graphene nano-platelets. In some embodiments, the micro-strain gauges comprise a conductive silicone composite loaded with carbon nanotubes. In some embodiments, the micro-strain gauges comprise a conductive silicone composite loaded with silver nanowires. In some embodiments, the micro-strain gauges comprise a conductive silicone composite loaded with gold nanowires. In some embodiments, the micro-strain gauges comprise a conductive silicone composite loaded with gold nanoparticles. In some embodiments, the micro-strain gauges comprise a conductive silicone composite loaded with copper nanowires.

In some embodiments, the micro-strain gauges are adapted to endure a strain of at least about 5%, or at least about 10%, or at least about 20%, or at least about 30%, or at least about 40%, or at least about 50%. In some embodiments, the micro-strain gauges are adapted to endure strains caused by contraction of healthy cardiomyocytes.

In some embodiments, the micro-strain gauges are adapted to detect deformation in one dimension. In some embodiments, the micro-strain gauges are adapted to detect deformation in two dimensions. In some embodiments, the micro-strain gauges are adapted to detect deformation in three dimensions. In some embodiments, the micro-strain gauges are adapted to detect deformation in all directions.

In some embodiments, the three-dimensional electronic scaffold comprises serpentine-shaped micro-strain gauges. In some embodiments, the three-dimensional electronic scaffold comprises lollipop-shaped micro-strain gauges. In some embodiments, the three-dimensional electronic scaffold comprises helix-shaped micro-strain gauges. In some embodiments, the three-dimensional electronic scaffold comprises convex-shaped micro-strain gauges. In some embodiments, the three-dimensional electronic scaffold comprises single-line-shaped micro-strain gauges. In some embodiments, the three-dimensional electronic scaffold comprises sinus-wave-shaped micro-strain gauges.

In some embodiments, the geometries and materials of the micro-strain gauges can be engineered to achieve minimal size as well as high sensing sensitivity and high durability.

In some embodiments, the micro-strain gauges are adapted to map intra-tissue cardiac contraction force. In some embodiments, the micro-strain gauges are adapted to map intra-tissue cardiac contraction force through an entire tissue construct in three dimensions. In some embodiments, the micro-strain gauges are adapted to map intra-tissue contractile pattern of a healthy cardiac tissue. In some embodiments, the micro-strain gauges are adapted to map intra-tissue contractile pattern of a diseased or damaged cardiac tissue.

In some embodiments, the three-dimensional electronic scaffold further comprises one or more microelectrodes adapted for detecting cardiac electrophysiology. In some embodiments, the microelectrodes are distributed spatially inside the porous scaffold.

In some embodiments, the three-dimensional electronic scaffold further comprises eukaryotic cells and/or prokaryotic cells disposed inside the porous scaffold and in contact with the micro-strain gauges. In some embodiments, the three-dimensional electronic scaffold further comprises mammalian cells disposed inside the porous scaffold and in contact with the micro-strain gauges. In some embodiments, the three-dimensional electronic scaffold further comprises murine cells disposed inside the porous scaffold and in contact with the micro-strain gauges. In some embodiments, the three-dimensional electronic scaffold further comprises human cells disposed inside the porous scaffold and in contact with the micro-strain gauges. In some embodiments, the three-dimensional electronic scaffold further comprises stem cells and/or progenitor cells disposed inside the porous scaffold and in contact with the micro-strain gauges.

In some embodiments, the three-dimensional electronic scaffold further comprises cardiomyocytes, cardiac stem cells and/or cardiac progenitor cells disposed inside the porous scaffold and in contact with the micro-strain gauges. In some embodiments, the three-dimensional electronic scaffold further comprises murine cardiomyocytes, cardiac stem cells and/or cardiac progenitor cells disposed inside the porous scaffold and in contact with the micro-strain gauges. In some embodiments, the three-dimensional electronic scaffold further comprises human cardiomyocytes, cardiac stem cells and/or cardiac progenitor cells disposed inside the porous scaffold and in contact with the micro-strain gauges.

In some embodiments, the three-dimensional electronic scaffold further comprises a beating cardiac tissue disposed inside the porous scaffold and in contact with the micro-strain gauges. In some embodiments, the three-dimensional electronic scaffold further comprises a beating murine cardiac tissue disposed inside the porous scaffold and in contact with the micro-strain gauges. In some embodiments, the three-dimensional electronic scaffold further comprises a beating human cardiac tissue disposed inside the porous scaffold and in contact with the micro-strain gauges.

Another aspect of some embodiments of the invention described herein relates to a method for fabricating the three-dimensional electronic scaffold described herein, comprising obtaining a plurality of micro-strain gauges on a porous scaffold by direct ink writing using a conductive ink, and curing the conductive ink. In some embodiments, the method comprises obtaining both the porous scaffold and the micro-strain gauges by direct ink writing.

Another aspect of some embodiments of the invention described herein relates to a method for fabricating the three-dimensional electronic scaffold described herein, comprising obtaining a plurality of micro-strain gauges on a porous scaffold by 3D printing using a conductive ink, and curing the conductive ink. In some embodiments, the method comprises obtaining both the porous scaffold and the micro-strain gauges by 3D printing.

A further aspect of some embodiments of the invention described herein relates to a method for culturing a cardiac tissue, comprising seeding one or more cardiac cells into the three-dimensional electronic scaffold described herein.

In some embodiments, the method comprises seeding one or more cardiac stem cells and/or cardiac progenitor cells into the three-dimensional electronic scaffold. In some embodiments, the method comprises seeding one or more mammalian cardiac stem cells and/or cardiac progenitor cells into the three-dimensional electronic scaffold. In some embodiments, the method comprises seeding one or more murine cardiac stem cells and/or cardiac progenitor cells into the three-dimensional electronic scaffold. In some embodiments, the method comprises seeding one or more human cardiac stem cells and/or cardiac progenitor cells into the three-dimensional electronic scaffold.

In some embodiments, the method further comprises differentiating cardiac stem cells and/or cardiac progenitor cells disposed inside the three-dimensional electronic scaffold into cardiomyocytes. In some embodiments, the method further comprises differentiating mammalian cardiac stem cells and/or cardiac progenitor cells disposed inside the three-dimensional electronic scaffold into cardiomyocytes. In some embodiments, the method further comprises differentiating murine cardiac stem cells and/or cardiac progenitor cells disposed inside the three-dimensional electronic scaffold into cardiomyocytes. In some embodiments, the method further comprises differentiating human cardiac stem cells and/or cardiac progenitor cells disposed inside the three-dimensional electronic scaffold into cardiomyocytes.

In some embodiments, the method further comprises differentiating cardiac stem cells and/or cardiac progenitor cells disposed inside the three-dimensional electronic scaffold into a beating cardiac tissue. In some embodiments, the method further comprises differentiating mammalian cardiac stem cells and/or cardiac progenitor cells disposed inside the three-dimensional electronic scaffold into a beating cardiac tissue. In some embodiments, the method further comprises differentiating murine cardiac stem cells and/or cardiac progenitor cells disposed inside the three-dimensional electronic scaffold into a beating cardiac tissue. In some embodiments, the method further comprises differentiating human cardiac stem cells and/or cardiac progenitor cells disposed inside the three-dimensional electronic scaffold into a beating cardiac tissue.

In some embodiments, the method further comprises exposing cardiac cells disposed inside the three-dimensional electronic scaffold to a drug compound. In some embodiments, the method further comprises exposing cardiac cells disposed inside the three-dimensional electronic scaffold to a biologic. In some embodiments, the method further comprises exposing cardiac cells disposed inside the three-dimensional electronic scaffold to a nucleic acid, a DNA, an RNA, an siRNA, an miRNA, a polypeptide, an antibody or fragment thereof, a cytokine, a growth factor, a toxin, a bacterial and/or a virus. In some embodiments, the method further comprises exposing the cardiac cells disposed inside the three-dimensional electronic scaffold to a transformation vector (e.g., a vector encoding a zinc finger protein, a transcription activator-like effector nucleases protein, or a CRISPR/Cas system).

In some embodiments, the method further comprises detecting contraction force of the cardiac cells by the micro-strain gauges. In some embodiments, the method further comprises detecting resistance changes of the micro-strain gauges.

In some embodiments, the resistance changes of the micro-strain gauges in real time can be quantitatively analyzed to obtain force, duration, frequency and synchronization of the contraction behavior of cardiac cells, through an entire tissue construct in three dimensions, under physiological conditions and/or with drug simulations.

In some embodiments, the method further comprises detecting cardiac electrophysiology of the cardiac cells by one or more microelectrodes.

An additional aspect of some embodiments of the invention described herein relates to a method comprising detecting and mapping intra-tissue cardiac contraction force of one or more cardiac cells or tissues disposed in a three-dimensional electronic scaffold, wherein the three-dimensional electronic scaffold comprises a porous scaffold and a plurality of micro-strain gauges distributed spatially inside the porous scaffold and in contact with the cardiac cells or tissues, and wherein the micro-strain gauges are adapted to detect contraction force of the cardiac cells or tissues.

These and other features, together with the organization and manner of operation thereof, will become apparent from the following detailed description when taken in conjunction with the accompanying drawings.

DETAILED DESCRIPTION

Reference will now be made in detail to some specific embodiments of the invention contemplated by the inventors for carrying out the invention. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims.

In the following description, numerous specific details are set forth in order to provide a thorough understanding of the present invention. Particular example embodiments of the present invention may be implemented without some or all of these specific details. In other instances, well known process operations have not been described in detail in order not to unnecessarily obscure the present invention.

Various techniques and mechanisms of the present invention will sometimes be described in singular form for clarity. However, it should be noted that some embodiments include multiple iterations of a technique or multiple instantiations of a mechanism unless noted otherwise.

Disclosed here is a novel device platform of a three-dimensional electronic scaffold (3DES) for generating 3D cardiac tissues and recording intra-tissue contraction force.

To address the need of fast and accurate in vitro models, a novel 3DES platform is developed that not only facilitate the generation of in vivo-like tissues, but also is capable of recording physiological functions in real time. The 3DES can be used to map intra-tissue cardiac contraction force. Such "smart" scaffold can assist mechanistic studies of fundamental cardiac research, pharmaceutical development, and regenerative medicine.

The 3DES can be built by the direct-ink writing technique pioneered by the LLNL (see Sullivan et al., *J. Phys. Chem. B*, 117:1686-1693 (2013)). The 3DES can be employed to record contraction forces inside a cardiac tissue down to single-cell level. Accordingly, one aspect of the invention relates to a 3DES which can be fabricated using tunable materials and structures. Another aspect of the invention relates to 3D-cultured cells and tissues using the 3DES. Another aspect of the invention relates to real-time recording of contraction of cardiac tissues grown from primary cardiomyocytes and/or cardiac stem cells.

Cardiac cells often adhere to the surface of a scaffold during their growth. When cells contract, the local scaffold network deforms accordingly. The degree of deformation (strain) can scale linearly with the contractile force. Accordingly, the 3DES can incorporate micro-strain gauges (a device that changes its resistivity quantitatively with strain) inside and as part of the scaffold to detect and monitor cardiac cell contraction.

Figure 1:
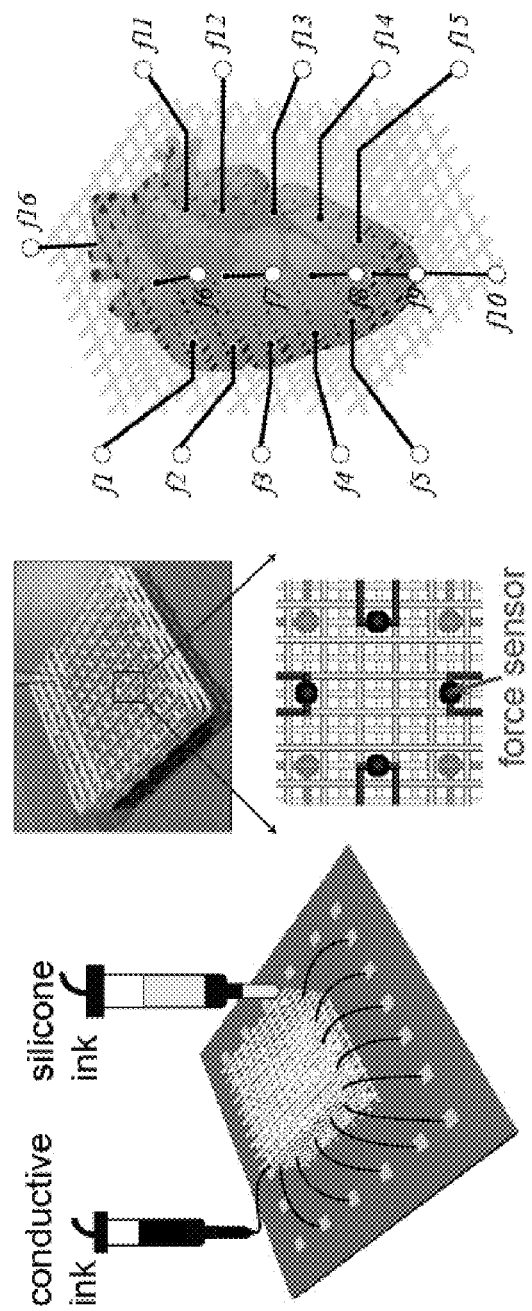
FIG. 1: Scheme of using 3D electronic scaffold with built-in force sensors to map intra-tissue cardiac contraction force.

Soft and biocompatible silicone ink can be used to construct the basic growth scaffold, and custom-made conductive silicone ink can be used to fabricate micro-strain gauges distributed spatially inside the scaffold. This can be achieved by computer-aided multi-material direct-ink writing technique, as shown in FIG. 1. The materials and geometries of strain gauges can be engineered to provide minimal size, high sensing sensitivity and high durability. The mechanical properties of the scaffold can be tailored by structural design to match the stiffness of natural cardiac tissue, in order to promote optimal tissue development. The ability to monitor cardiac cell contraction in in vivo-like cardiac tissues can provide precise tissue models for the understanding of heart damage development and remodeling and the mechanisms of cardiac regeneration.

Elastic and Conductive Ink.

Figure 2:
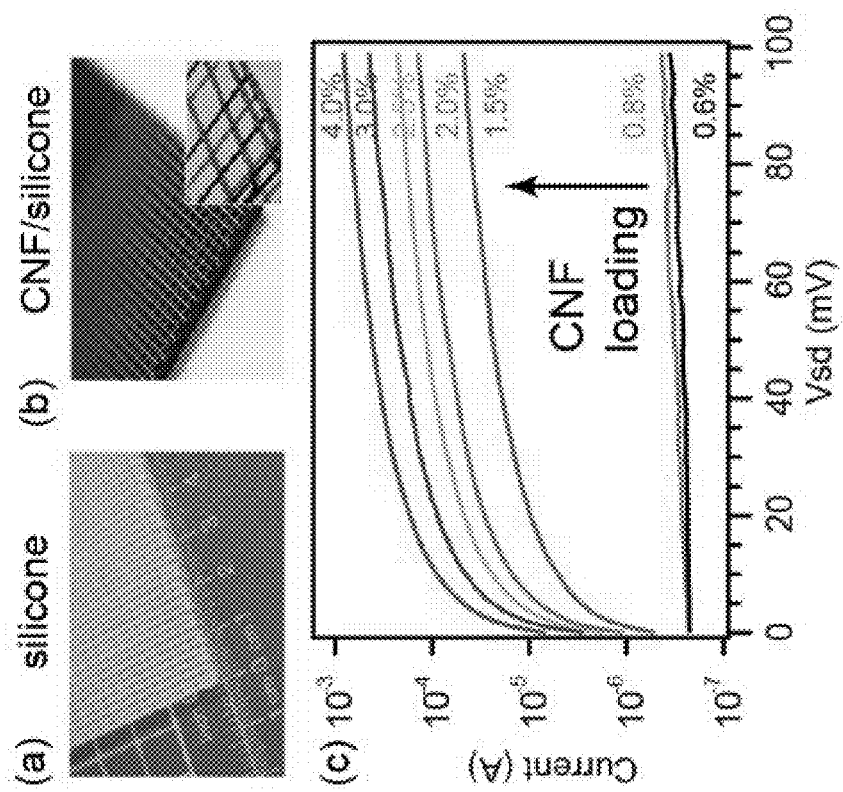
FIG. 2: (a) A silicone scaffold and (b) a CNF/silicone scaffold fabricated by direct ink writing; (c) I-V data showing the conductance of CNF/silicone inks increase with increasing amounts of CNF loading.

The "writing" of cardiac strain gauges requires a suitable ink material of good electrical conductivity, biocompatibility, and appropriate rheological properties. Conventional strain gauges made of rigid metals/semiconductors can only sustain small strain of <0.5%. However, because healthy cardiomyocytes can shorten up to 40% during contraction, the cardiac strain gauge should be able to endure large strains. To address this issue, an elastic and conductive ink material using silicone composited with carbon nanofiber (CNF) has been developed. Both silicone and CNF are biocompatible. As shown in FIG. 2b, the electrical conductivity of the ink increased almost four orders of magnitude when the CNF loading increased from 0.6% to 4%, while the elasticity only moderately decreased. Balancing the electrical conductivity, rheology and stretchability of the ink can optimize its use for fabricating micro-strain gauges.

2D/3D Strain Gauges.

Figure 3:
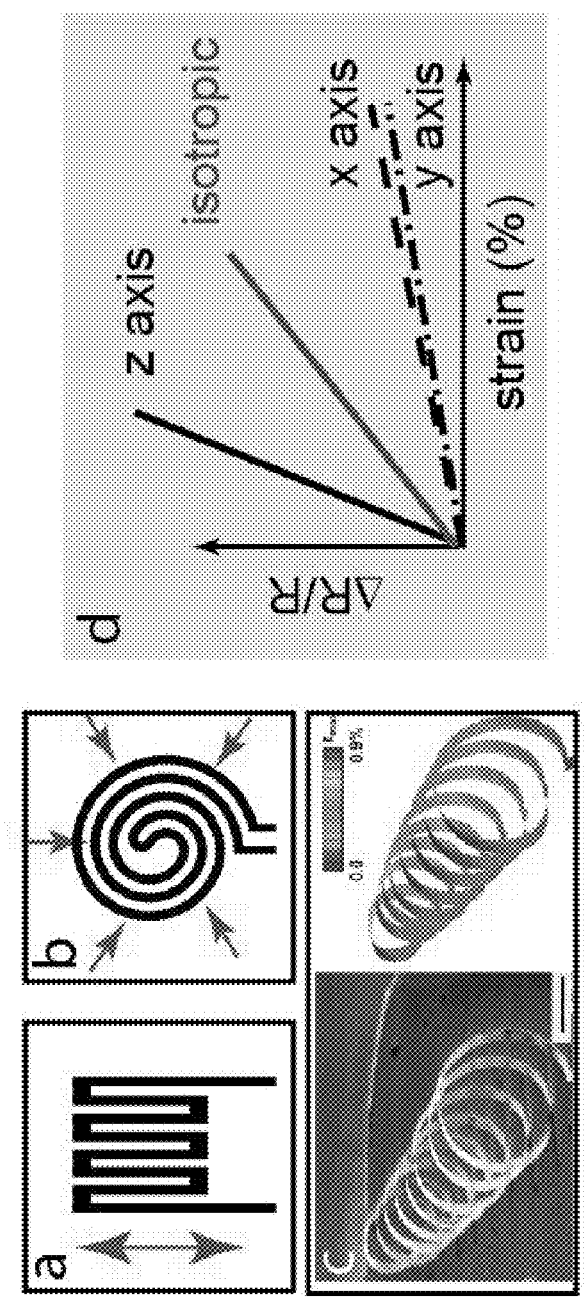
FIG. 3: (a,b) 2D and (c) 3D gauge geometries; (d) example gauge factor of helix sensors.

A strain gauge carries a strain sensitive pattern, such as serpentine (see FIG. 3a). Is resistance, R, is determined by the device shape and the metal resistivity ($\rho$), according to $R=\rho(L/A)$, where A and L are the cross-sectional area and effective length, respectively, of the electrical path. Once a tensile (or compressive) strain, $\varepsilon$, is applied along the longitudinal axis (FIG. 3a), L is increased (or decreased) due to the shape change, yielding a linearly increased (or decreased) resistance change, ΔR. The sensitivity of a strain gauge can be assessed by gauge factor (GF), where GF=(ΔR/R)/ε. The serpentine shape only senses strain in a longitudinal direction. In order to record local force generation in all three dimensions inside a beating cardiac tissue, gauge geometries with suitable electrical properties, sensitivity, hysteresis and durability can be fabricate with DIW. For example, while serpentine-shaped and lollipop-shaped MSGs can detect strain in 1D and 2D, respectively (see FIGS. 3a and 3b), helix-shaped MSG can detect strain in 3D and detect deformation in all directions (see FIG. 3c). Finite-element analysis can be used to analyze the out-of-plane bending strain under an applied force, in order to correlate force and strain with electrical conductance in unique 3D device geometries.

Structure and Mechanical Properties of 3DES.

The stiffness of the overall scaffold can influence cell shape, protein expression and tissue organization. Previous cardiac research has shown that cardiomyocytes retain the best contractile phenotype on matrices that mimic the compliance of natural heart tissues (see Bhana et al., *Biotechnol. Bioeng.*, 105:1148-1160 (2009)). To promote cardiac growth and functioning, the Young's modulus of the 3DES can be matched with that of healthy myocardium (e.g., 10-15 kPa). This can be done by tuning the porosity of the scaffold structure, as stiffness and porosity are correlated via $E'=E(1-(p/pc))^f$, where E' and E are the effective Young's modulus of porous and solid materials, respectively, P is the porosity, f is an experimental fitting parameter.

Cell/Tissue Culture on 3DES.

Mammalian cardiac cells and tissues, including murine and human cardiac cells and tissues, can be cultured on the 3DES. In one example, primary rat cardiomyocytes as a model system can be cultured onto the 3DES using known protocols (see Timko et al., *Nano. Lett.*, 9:914-8 (2009)). The 3D-cultured cells and tissues can exhibit spontaneous beating associated with action potential generation, form cardiac patches, and show contraction synchronization as a result of good intercellular communication.

In another example, the 3DES can be used to culture a subpopulation of stem/progenitor cells within adult myocardium characterized by a distinct Hoechst dye efflux pattern on FACS analysis. These progenitor cells are capable of differentiation into functional cardiomyocytes and are useful in tissue regeneration for clinical applications (see Unno et al., *Circ. Res.*, 110:1355-63 (2012); Pfister et al., *Transl. Res.*, 163:307-320 (2014)).

The 3DES can be employed to perform multiplex recording of contractile force of side progenitor cells induced cardiac tissues. Cardiac progenitor cells can be cultured onto the 3DES and induced to differentiate using known protocol (see Unno et al., *Circ. Res.*, 110:1355-63 (2012)). After a few days these cells can self-assemble into functional cardiac micro-tissues and start to beat regularly, straining the scaffold and generating electrical readout through the strain gauge matrix. By quantitative analysis of the resistance change of the gauges in real time, force, duration, frequency and synchronization of the contraction behavior of progenitor cell-induced cardiomyocytes can be obtained, throughout the entire tissue construct in three dimensions, under physiological conditions and/or with drug stimulation.

Applications of 3DES.

The 3DES described herein can be used in a variety of applications. For example, they can be used in in-vitro culture, drug screening, pharmaceutical testing, tissue surrogates, drug delivery, toxicology test, pharmacology test, electrical stimulation and recording, optical imaging, cardiac beating assay, and human-relevant tissue models for drug testing.

WORKING EXAMPLES

Fabrication of 3D Printed Electronic Scaffold for Cardiac Force Measurement.

This electronic scaffold is designed for measurement of contraction force of 3D-cultured cardiac tissue. The scaffold comprises a 3D-printed silicone filament network, and 3D-printed conductive silicone (silicone mixed with carbon nanofiber filler) micro-strain gauges. The fabrication procedure includes the following:

1. Prepare silicone ink. Mix silicone base with catalyst at 10:1 ratio. Mix well.

2. Prepare conductive silicone ink.

2.1. Dissolve 4 g silicone base in 10 ml chloroform, stirring overnight. Screw tight the cap to prevent CHCl3 evaporation.

2.2. Add carbon nanofiber and silicone catalyst in 10 ml chloroform, sonicate overnight to ensure good dispersion. Screw tight the cap to prevent $CHCl_3$ evaporation.

2.3. Mix the above two compositions, remove the cap, stir at room temperature until $CHCl_3$ is fully evaporated.

3. Print underlying silicone scaffold using a direct ink writer. Print 5-10 layers. Cure on a hotplate at 180° C. for an hour.

4. Print the layer of strain gauge with conductive silicone ink. Make sure the filaments that compose strain gauge are printed on top of the corresponding silicone filaments. Cure on a hotplate at 180° C. for an hour.

5. Print top silicone scaffold using a direct ink writer. Print 5-10 layers. Cure on a hotplate at 180° C. for an hour.

The conductivity and rheology of the conductive silicone ink can be tune by varying the loading ratio of carbon nanofiber to meet specific needs.

As used herein, the singular terms "a," "an," and "the" include plural referents unless the context clearly dictates otherwise. Thus, for example, reference to a compound can include multiple compounds unless the context clearly dictates otherwise.

As used herein, the terms "substantially," "substantial," and "about" are used to describe and account for small variations. When used in conjunction with an event or circumstance, the terms can refer to instances in which the event or circumstance occurs precisely as well as instances in which the event or circumstance occurs to a close approximation. For example, the terms can refer to less than or equal to ±10%, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations, which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scopes of this invention.

What is claimed is:

1. A three-dimensional electronic scaffold, comprising a porous scaffold and a plurality of micro-strain gauges distributed spatially inside the porous scaffold, wherein the micro-strain gauges comprise a conductive silicone composite and are adapted to detect cardiac contraction force by detecting resistance change of each micro-strain gauge caused by the cardiac contraction force.

2. The three-dimensional electronic scaffold of claim 1, wherein the porous scaffold comprises silicone.

3. The three-dimensional electronic scaffold of claim 1, wherein the porous scaffold has a Young's modulus of about 10 kPa to about 15 kPa.

4. The three-dimensional electronic scaffold of claim 1, wherein the micro-strain gauges comprise a conductive silicone composite loaded with carbon nanofiber.

5. The three-dimensional electronic scaffold of claim 1, wherein the micro-strain gauges comprise a conductive silicone composite loaded with at least about 1.5 wt. % of carbon nanofiber.

6. The three-dimensional electronic scaffold of claim 1, wherein the micro-strain gauges are adapted to endure a strain of at least about 5%.

7. The three-dimensional electronic scaffold of claim 1, wherein the micro-strain gauges are adapted to detect deformation in all directions.

8. The three-dimensional electronic scaffold of claim 1, wherein the micro-strain gauges are adapted to map intra-tissue cardiac contraction force.

9. The three-dimensional electronic scaffold of claim 1, further comprising one or more microelectrodes adapted for detecting cardiac electrophysiology.

10. The three-dimensional electronic scaffold of claim 1, further comprising cardiomyocytes, cardiac stem cells and/or cardiac progenitor cells disposed inside the porous scaffold and in contact with the micro-strain gauges.

11. The three-dimensional electronic scaffold of claim 1, further comprising a beating cardiac tissue disposed inside the porous scaffold and in contact with the micro-strain gauges.

12. A method for culturing a cardiac tissue, comprising seeding one or more cardiac cells into the three-dimensional electronic scaffold of claim 1.

13. The method of claim 12, wherein the cardiac cells comprise cardiac stem cells and/or cardiac progenitor cells.

14. The method of claim 13, further comprising differentiating the cardiac stem cells and/or cardiac progenitor cells into cardiomyocytes.

15. The method of claim 13, further comprising differentiating the cardiac stem cells and/or cardiac progenitor cells into a beating cardiac tissue.

16. The method of claim 12, further comprising stimulating the cardiac cells with a drug compound.

17. The method of claim 12, further comprising detecting contraction force of the cardiac cells by the micro-strain gauges.

18. The method of claim 12, further comprising detecting cardiac electrophysiology of the cardiac cells by one or more microelectrodes.

19. A method comprising detecting and mapping intra-tissue cardiac contraction force of one or more cardiac cells or tissues disposed in a three-dimensional electronic scaffold, wherein the three-dimensional electronic scaffold comprises a porous scaffold and a plurality of micro-strain gauges distributed spatially inside the porous scaffold and in contact with the cardiac cells or tissues, and wherein the micro-strain gauges comprise a conductive silicone composite and are adapted to detect contraction force of the cardiac cells or tissues.

* * * * *